United States Patent
Lee et al.

(10) Patent No.: US 11,164,868 B2
(45) Date of Patent: Nov. 2, 2021

(54) SEMICONDUCTOR DEVICE

(71) Applicant: Taiwan Semiconductor Manufacturing Co., Ltd., Hsinchu (TW)

(72) Inventors: Hsin-Yi Lee, Hsinchu (TW); Cheng-Lung Hung, Hsinchu (TW); Weng Chang, Hsin-Chu (TW); Chi-On Chui, Hsinchu (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 0 days.

(21) Appl. No.: 16/777,831

(22) Filed: Jan. 30, 2020

(65) Prior Publication Data

US 2021/0091077 A1 Mar. 25, 2021

Related U.S. Application Data

(60) Provisional application No. 62/905,280, filed on Sep. 24, 2019.

(51) Int. Cl.
*H01L 27/088* (2006.01)

(52) U.S. Cl.
CPC .............. *H01L 27/0886* (2013.01)

(58) Field of Classification Search
CPC .......... H01L 27/0886; H01L 27/092; H01L 29/6681
See application file for complete search history.

(56) References Cited

U.S. PATENT DOCUMENTS

| | | | |
|---|---|---|---|
| 8,836,016 B2 | 9/2014 | Wu et al. | |
| 8,841,701 B2 | 9/2014 | Lin et al. | |
| 8,847,293 B2 | 9/2014 | Lee et al. | |
| 8,853,025 B2 | 10/2014 | Zhang et al. | |
| 8,962,400 B2 | 2/2015 | Tsai et al. | |
| 9,093,514 B2 | 7/2015 | Tsai et al. | |
| 9,236,267 B2 | 1/2016 | De et al. | |
| 9,245,805 B2 | 1/2016 | Yeh et al. | |
| 9,520,482 B1 | 12/2016 | Chang et al. | |
| 9,576,814 B2 | 2/2017 | Wu et al. | |
| 10,014,185 B1* | 7/2018 | Wu | H01L 21/02186 |
| 2013/0299914 A1* | 11/2013 | Kim | H01L 21/823821 257/369 |
| 2014/0252487 A1* | 9/2014 | Stephens | H01L 27/092 257/368 |
| 2016/0020118 A1* | 1/2016 | Park | H01L 27/092 438/592 |

(Continued)

*Primary Examiner* — Changhyun Yi
(74) *Attorney, Agent, or Firm* — JCIPRNET

(57) ABSTRACT

A semiconductor device may include a substrate, a first transistor disposed on the substrate, and a second transistor disposed on the substrate. The first gate structure of the first transistor may include a first high-k layer, a first capping layer and a first work function layer sequentially disposed on the substrate. A material of the first work function layer includes Ta. The second transistor includes a second gate structure. The second gate structure includes a second high-k layer, a second capping layer and a second work function layer sequentially disposed on the substrate. The first capping layer and the second capping layer are formed of the same layer, and a material of the second work function layer is different from the material of the first work function layer.

20 Claims, 9 Drawing Sheets

(56) References Cited

U.S. PATENT DOCUMENTS

2016/0307896 A1* 10/2016 Lin .................. H01L 29/42364
2017/0330829 A1* 11/2017 Wu .................. H01L 21/76861
2018/0261677 A1* 9/2018 Lee ................. H01L 21/823842

* cited by examiner

SEMICONDUCTOR DEVICE

CROSS-REFERENCE TO RELATED APPLICATION

This application claims the priority benefits of U.S. provisional application Ser. No. 62/905,280, filed on Sep. 24, 2019. The entirety of the above-mentioned patent application is hereby incorporated by reference herein and made a part of this specification.

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (e.g., the number of interconnected devices per chip area) has generally increased while geometry size (e.g., the smallest component (or line) that can be created using a fabrication process) has decreased. This scaling down process generally provides benefits by increasing production efficiency and lowering associated costs. However, scaling down has also led to challenges that may not have been presented by previous generations at larger geometries.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
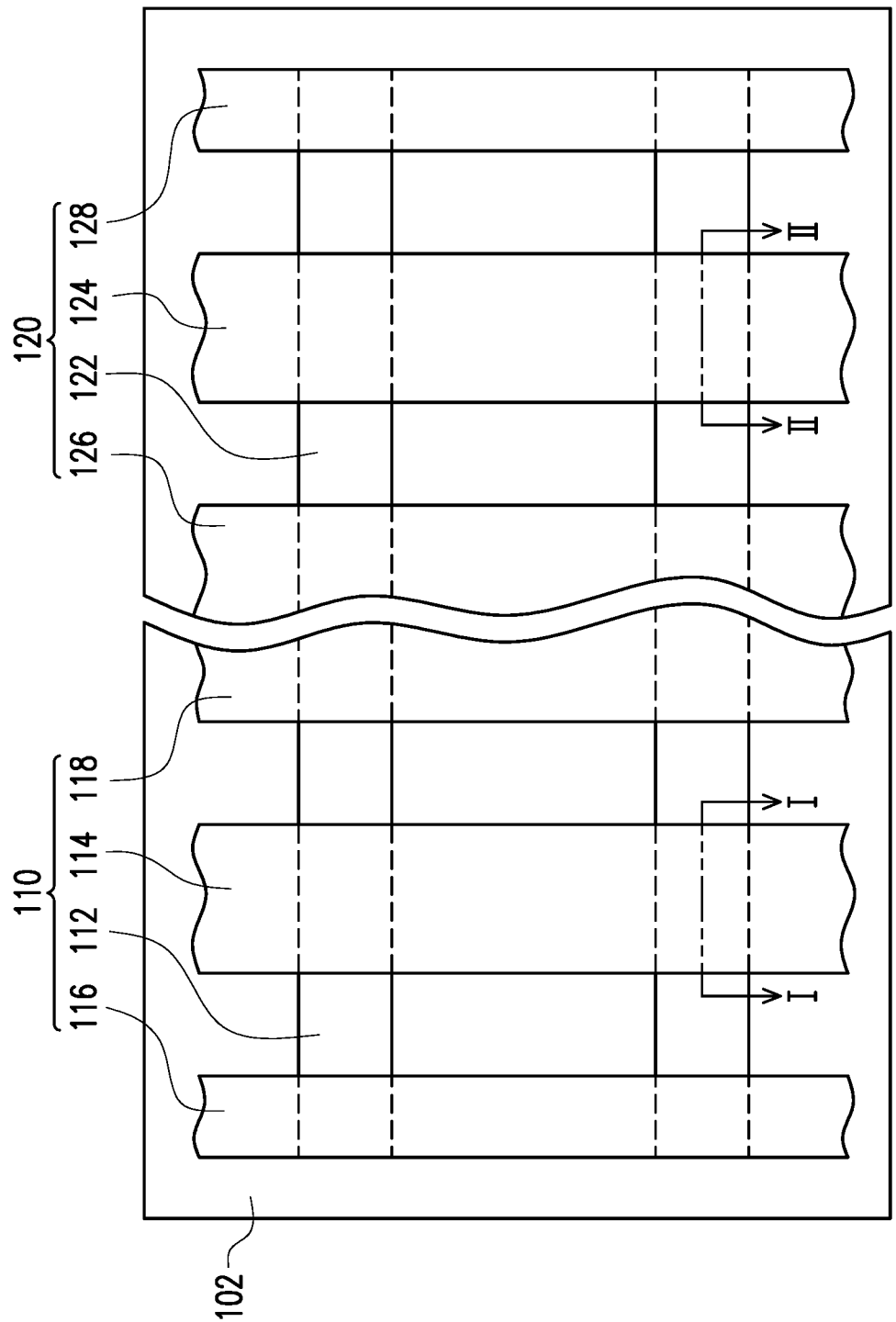
FIG. 1 schematically illustrates a plan view of a semiconductor device in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Embodiments of the present disclosure may be used to form gate stacks suitable for use in planar bulk metal-oxide-semiconductor field-effect transistors (MOSFETs), multi-gate transistors (planar or vertical) such as FinFET devices, gate-all-around (GAA) devices, Omega-gate (a-gate) devices, or Pi-gate (H-gate) devices, as well as strained-semiconductor devices, silicon-on-insulator (SOI) devices, partially-depleted SOI devices, fully-depleted SOI devices, or other devices as known in the art. In addition, embodiments disclosed herein may be employed in the formation of P-type and/or N-type devices. One of ordinary skill may recognize other embodiments of semiconductor devices that may benefit from aspects of the present disclosure. For example, some embodiments as described herein may also be applied to the formation of contacts, vias, or interconnects.

The fins may be patterned by any suitable method. For example, the fins may be patterned using one or more photolithography processes, including double-patterning or multi-patterning processes. Generally, double-patterning or multi-patterning processes combine photolithography and self-aligned processes, allowing patterns to be created that have, for example, pitches smaller than what is otherwise obtainable using a single, direct photolithography process. For example, in one embodiment, a sacrificial layer is formed over a substrate and patterned using a photolithography process. Spacers are formed alongside the patterned sacrificial layer using a self-aligned process. The sacrificial layer is then removed, and the remaining spacers, or mandrels, may then be used to pattern the fins.

FIG. 1 schematically illustrates a plan view of a semiconductor device in accordance with some embodiments. Referring to FIG. 1, a semiconductor device 100 may include a substrate 102, a first transistor 110, and a second transistor 120. The first transistor 110 and the second transistor 120 are disposed on the substrate 102. In some embodiments, the semiconductor device 100 may be an integrated circuit device typically provided in chip form and may be encapsulated in a package. The semiconductor device 100 may include more than two transistors while the first transistor 110 and the second transistor 120 are illustrated as examples without the intention of limiting the numbers of the transistors in the semiconductor device 100. In the semiconductor device 100, thousands, or more, transistors may be interconnected. In some embodiments, the first transistor 110 and the second transistor 120 may have different device characteristics and thus be able to provide various functions. For example, the first transistor 110 and the second transistor 120 may each be p-type transistor or n-type transistor. In accordance with some embodiments, one or more n-type transistor in the semiconductor device 100 may be interconnected with one or more p-type transistor, for example, by sharing a common gate structure, or may be connected by metal contacts (not shown).

The substrate 102 may be a bulk semiconductor substrate such as a bulk silicon wafer. The term "substrate" may be used to refer to just the semiconductor substrate or a semiconductor substrate inclusive of isolation regions. The substrate 102 may be or include any silicon-containing substrate including, but not limited to, single crystal Si, polycrystalline Si, amorphous Si, or Si-on-insulator (SOI) substrates and the like, and may be n-type or p-type doped as desired for a particular application. The substrate 102 may also include other semiconductors such as germanium, silicon carbide (SiC), silicon germanium (SiGe), or diamond. Alternatively, the substrate 102 may include a compound semiconductor and/or an alloy semiconductor. Further, in some embodiments, the substrate 102 may include an epitaxial layer (epi-layer). The substrate 102 may have one or more fin or fin-like structures for constructing the transistors such as the first transistor 110 and the second transistor 120. The first transistor 110 and the second transistor 120 may be fin type field effect transistors (Fin FETs).

The first transistor 110 may include a first semiconductor fin 112, a first gate structure 114, a first source 116 and a first drain 118. In some embodiments, the first transistor 110 may include two or more first semiconductor fins 112 and each of the first semiconductor fins 112 may be a linear structure on the substrate 102. The first semiconductor fins 112 may be located between neighboring isolation regions in the substrate 102 in some embodiments. The first gate structure 114 is disposed over the first semiconductor fins 112. The first gate structure 114 may extend in a direction intersecting the extending direction of each of the first semiconductor fins 112 and cross through the first semiconductor fins 112. The first source 116 and the first drain 118 are located at two opposite sides of the first gate structure 114, and the first semiconductor fins 112 connect between the first source 116 and the first drain 118.

The second transistor 120 may have a top view structure similar to the first transistor 110. The second transistor 120 may include a second semiconductor fin 122, a second gate structure 124, a second source 126, and a second drain 128. In some embodiments, the second transistor 120 may include two or more second semiconductor fins 122 and each of the second semiconductor fins 122 may be a linear structure on the substrate 102. The second gate structure 124 is disposed over the second semiconductor fins 122. The second gate structure 124 may extend in a direction intersecting the extending direction of each of the second semiconductor fins 122 and cross through the second semiconductor fins 122. The second source 126 and the second drain 128 are located at two opposite sides of the second gate structure 124, and the second semiconductor fins 122 connect between the second source 126 and the second drain 128.

Figure 2:
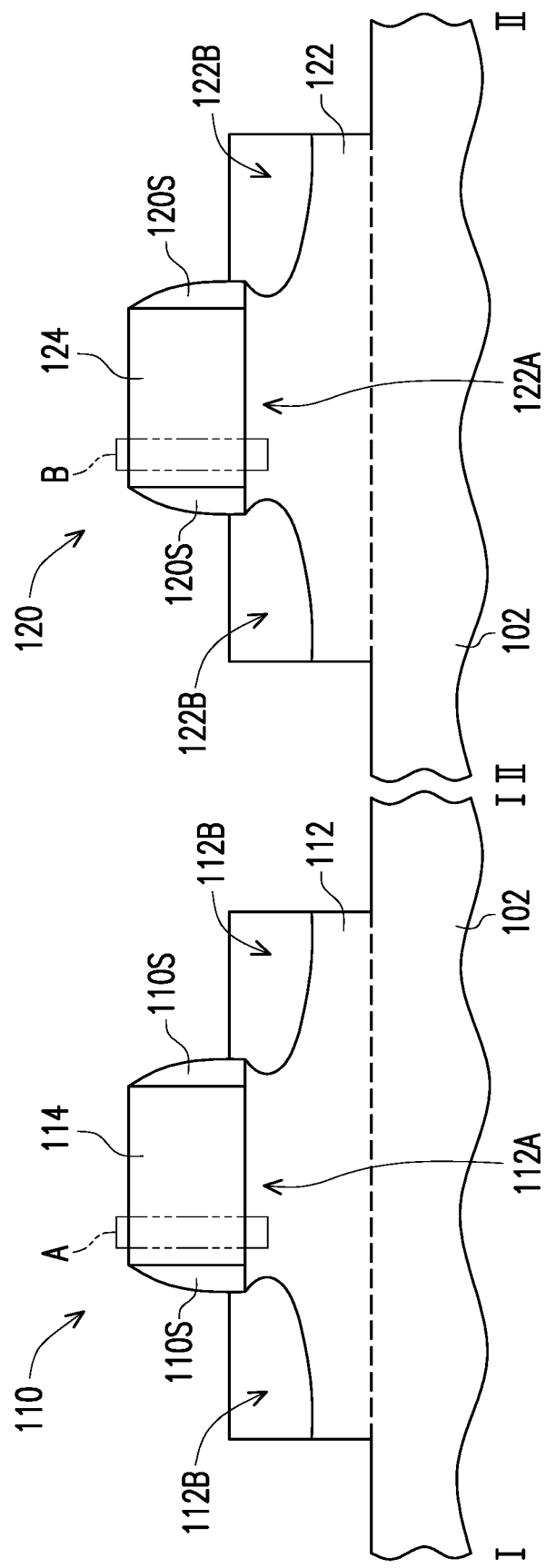
FIG. 2 schematically illustrates a cross-sectional view of a semiconductor device taken along lines I-I and II-II in FIG. 1.

FIG. 2 schematically illustrates a cross-sectional view of a semiconductor device taken along lines I-I and II-II in FIG. 1. Referring to FIG. 2, the first semiconductor fin 112 and the second semiconductor fin 122 may be protruded structures on the substrate 102. A spacer 110S and a spacer 120S may be further disposed on the substrate 102 and formed along sidewalls of first gate structure 114 and the second gate structure 124. The spacer 110S and the spacer 120S each may include one or more layers and may be made of silicon nitride, silicon oxynitride, silicon carbon nitride, the like, multi-layers thereof, or a combination thereof. The spacer 110S is disposed on the first semiconductor fin 112 to define a recess structure on the substrate 102 with the first semiconductor fin 112. The first gate structure 114 is disposed in the recess structure and surrounded by the spacer 110S.

Similarly, the spacer 120S may define a recess structure on the second semiconductor fin 122 and the second gate structure 124 may be disposed in the recess structure and surrounded by the spacer 120S.

In some embodiments, the first semiconductor fin 112 may have a channel region 112A. Two doped regions 112B may be formed and located at opposite sides of the channel region 112A. Similarly, in the second transistor 120, the second semiconductor fin 122 may have a channel region 122A and there are two doped regions 122B respectively located at opposite sides of the channel region 122A. The doped regions 112B and 122B may include or be silicon germanium, silicon carbide, silicon phosphorus, pure or substantially pure germanium, a III-V compound semiconductor, a II-VI compound semiconductor, or the like. The doped regions 112B and 122B may be raised in relation to the channel region 112A in some embodiments. The doped regions 112B and 122B may be formed by epitaxial growth, and possibly with implantation, on opposing sides of the respective gate stacks (e.g. the first gate structure 114 and the second gate structure 124). The doped regions 112B and 122B may be doped by in situ doping during the epitaxial growth and/or by implantation after the epitaxial growth.

In some embodiments, the doped regions 112B and the doped regions 122B may include p-type dopant material such as boron, aluminum, gallium, indium, or the like, or n-type dopant material such as phosphorus, arsenic, antimony, bismuth, lithium or the like. In some embodiments, lightly doped source/drain (LDD) regions (not shown) may be respectively disposed between the channel region 112A and the doped regions 112B and between the channel region 122A and the doped regions 122B, while the LDD regions may have a dopant concentration less than the doped regions 112B and 122B. In some embodiments, the dopant material of the doped region 112A and the dopant material of the doped region 122B may be different. In some embodiments, one of the first transistor 110 and the second transistor 120 may be p-type transistor and the other one may be n-type transistor corresponding to the types of the dopant materials in the doped regions 112B and 122B. Or, the first transistor 110 and the second transistor 120 may both be the same type transistors with different threshold voltages.

Figure 3:
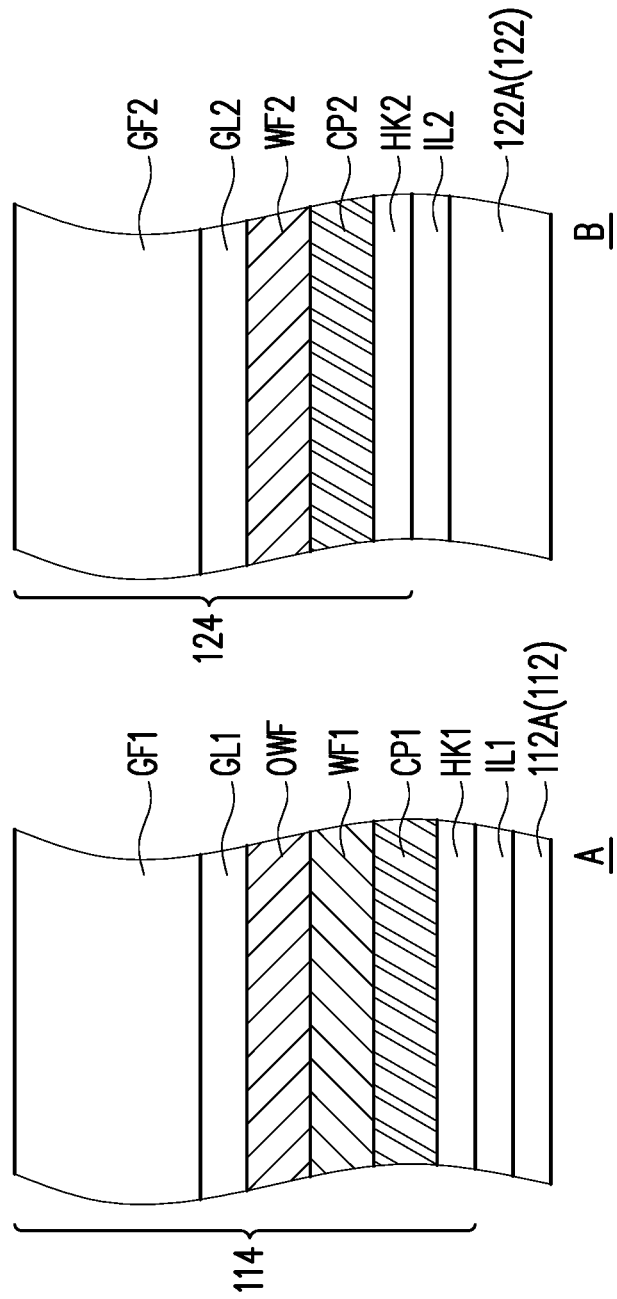
FIG. 3 schematically illustrates enlarged views of the portion A and the portion B in FIG. 2 in accordance with some embodiments.

FIG. 3 schematically illustrates enlarged views of the portion A and the portion B in FIG. 2 in accordance with some embodiments. As shown in FIGS. 2 and 3, the portion A presents an enlarged portion of the first gate structure 114 and the portion B presents an enlarged portion of the second gate structure 124. In the first transistor 110, an insulating layer IL1 is disposed on the channel region 112A and between the first semiconductor fin 112 and the first gate structure 114. Similarly, in the second transistor 120, an insulating layer IL2 is disposed on the channel region 122A and between the second semiconductor fin 122 and the second gate structure 124. The insulating layer IL1 and the insulating layer IL2 may be deposited or thermally grown respectively on the first semiconductor fin 112 and the second semiconductor fin 122 according to acceptable techniques, and made of, for example, silicon dioxide, a low-k dielectric material (e.g., a material having a dielectric constant lower than silicon dioxide), silicon oxynitride, phosphosilicate glass (PSG), borosilicate glass (BSG), borophosphosilicate glass (BPSG), undoped silicate glass (USG), fluorinated silicate glass (FSG), organosilicate glasses (OSG), $SiO_xC_y$, Spin-On-Glass, Spin-On-Polymers, silicon carbon material, a compound thereof, a composite thereof, the like, or a combination thereof.

In the portion A, the first gate structure 114 may include a first high-k layer HK1, a first capping layer CP1, a first work function layer WF1, an overlying work function layer OWF, a first glue layer GL1 and a first gate fill material GF1 sequentially disposed on the insulating layer IL1. Each of the first high-k layer HK1, the first work function layer WF1, the overlying work function layer OWF, the first glue layer GL1 and the first gate fill material GF1 may be deposited and/or formed by using physical vapor deposition (PVD), Molecular-Beam Deposition (MBD), atomic layer deposition (ALD), chemical vapor deposition (CVD), sputtering, or other known processes.

Similarly, in the portion B, the second gate structure 124 is disposed on the insulating layer IL2 and may include a second high-k layer HK2, a second capping layer CP2, a second work function layer WF2, a second glue layer GL2 and a second gate fill material GF2. The second high-k layer HK2, the second work function layer WF2, the second glue layer GL2 and the second gate fill material GF2 may be sequentially deposited on the insulating layer IL2. Each of the second high-k layer HK2, the second work function layer WF2, the second glue layer GL2 and the second gate fill material GF2 may be deposited by using physical vapor deposition (PVD), Molecular-Beam Deposition (MBD), atomic layer deposition (ALD), chemical vapor deposition (CVD), sputtering, or other known processes, depending on the material composition of the layer.

In some embodiments, the first high-k layer HK1 and the second high-k layer HK2 are formed by a common high-k material layer. The formation methods of the common high-k material layer may include Molecular-Beam Deposition (MBD), ALD, PECVD, and the like. The common high-k material layer may have a dielectric constant greater than, for example, about 3.9 (the dielectric constant of silicon dioxide) or greater than about 7.0, and be made of, but not limited to, a metal oxide or a silicate of Hf, Al, Zr, La, Mg, Ba, Ti, Pb, and combinations thereof. Alternatively, the common high-k material layer may include other high-k dielectrics, such as $TiO_2$, HfZrO, $Ta_2O_3$, $HfSiO_4$, $ZrO_2$, $ZrSiO_2$, LaO, AlO, ZrO, TiO, $Ta_2O_5$, $Y_2O_3$, $SrTiO_3$ (STO), $BaTiO_3$ (BTO), BaZrO, HfZrO, HfLaO, HfSiO, LaSiO, AlSiO, HfTaO, HfTiO, (Ba, Sr) $TiO_3$ (BST), $Al_2O_3$, $Si_3N_4$, oxynitrides (SiON), combinations thereof, or other suitable material.

In some embodiments, one or more capping layer such as the first capping layer CP1 and the second capping layer CP2 may be disposed on the first high-k layer HK1 and the second high-k layer HK2 to protect from damages of the first high-k layer HK1 and the second high-k layer HK2 during subsequent processing steps. The first capping layer CP1 and the second capping layer CP2 may prevent from the material diffusion from the overlying layers to the first high-k layer HK1 and the second high-k layer HK2 so that the dielectric property of the first high-k layer HK1 and the second high-k layer HK2 may be ensured. The material of the first capping layer CP1 and the second capping layer CP2 may include nitride, silicon nitride, carbon nitride, and/or aluminum nitride of titanium; a nitride, carbon nitride, and/or carbide of tungsten; the like; or a combination thereof. In some embodiments, the material of the first capping layer CP1 and the second capping layer CP2 may include titanium silicon nitride (TSN), titanium nitride (TiN), or the like. The first capping layer CP1 and the second capping layer CP2 may be formed of the same layer and have substantially the same thickness.

The first work function layer WF1 may be in direct contact with the first capping layer CP1 in the first gate structure 114 and the overlying work function layer OWF may be disposed on the first work function layer WF1, such that the first work function layer WF1 is positioned between the overlying work function layer OWF and the first capping layer CP1. The second work function layer WF2 may be in direct contact with the second capping layer CP2. A material of the first work function layer WF1 may be different from a material of the second work function layer WF2. A material of the overlying work function layer OWF and the material of the second work function layer WF2 may be the same. In some embodiments, the overlying work function layer OWF and the second work function layer WF2 may be of the same layer.

In some embodiments, during fabrication of the semiconductor device having the first transistor 110 and the second transistor 120, the material layer for forming the first work function layer WF1, such as TaN may be deposited on the substrate 102 to cover the region of the first gate structure 114 and also the region of the second gate structure 124 using atomic layer deposition (ALD) process. Subsequently, the TaN material layer may be patterned by removing the portion of the TaN layer covering on the region of the second gate structure 124 by using a halogen based etchant such as Cl-based or F-based etchant. In some embodiments, the Cl-based or F-based etchant may include $TiCl_x$, $TaCl_x$, $TiF_x$, $HfCl_x$, $WF_x$, or $WCl_x$, where 'x' is equal to about 1-6. During the patterning process, the portion of the TaN material layer covering the second capping layer CP2 may be removed by the halogen based etchant until the second capping layer CP2 is exposed. In some embodiments, the material of the first work function layer WF1 has a higher etching rate for the halogen based etchant than the material of the second capping layer CP2. The resistance of the material of the second capping layer CP2 with respect to the halogen based etchant may be sufficiently high to be hardly removed during the patterning process of the TaN material layer. Thus, the TaN material layer may be patterned to form the first work function layer WF1 on the first capping layer CP1 without damaging the second capping layer CP2, and the material of the first work function layer WF1 may include TaN. In some alternative embodiments, the material of the first work function layer WF1 may include HfN, WN, or the like. In some embodiments, the material of the second high-k layer HK2 presents an etching rate for a halogen based etchant such as $WCl_5$ between the material of the first work function layer WF1 and the material of the second capping layer CP2. The second capping layer CP2 may serve as an etching stop layer during the patterning of the TaN material layer such that the second high-k layer HK2 may not be damaged during the patterning process.

Subsequently, the material of the second work function layer WF2 and the overlaying work function layer OWF may be deposited on the exposed second capping layer CP2 and the first work function layer WF1 using, for example, ALD process. The second work function layer WF2 may be in direct contact with the second capping layer CP2 and the overlying work function layer OWF may be in direct contact with the first work function layer WF1. In some embodiments, the material of the second work function layer WF2 and the overlaying work function layer OWF may include Al such as TiAl, TiAlC, etc. The first work function WF1 in direct contact with the first capping layer CP1 and the overlying work function layer OWF stacking on the first work function layer WF1 may together provide the work function tuning effect in the first transistor 110. The second work function layer WF2 in direct contact with the second capping layer CP2 may provide the work function tuning effect in the second gate structure 124. Since the first transistor 110 and the second transistor 120 include different work function tuning structures, the electricity property of the first transistor 110 and the second transistor 120 may be different. For example, the threshold voltage of the first transistor 110 may be different from that of the second transistor 120. Alternatively, one of the first transistor 110 and the second transistor 120 may be a p-type device while the other is an n-type device. In some embodiments, the first transistor 110 having the first work function layer WF1 and the overlying work function layer OWF may be a p-type device and the second transistor 120 having the second work function layer WF2 may be an n-type device. In some embodiments, first work function layer WF1 may include metals having a work function substantially aligned with a work function of the substrate valence band, or at least substantially aligned with a work function of the valence band of the channel region 112A of the first transistor 110 and the first transistor 110 may serve as a P-type transistor. The second work function layer WF2 may include metals having a work function substantially aligned with a work function of the substrate conduction band, or at least substantially aligned with a work function of the conduction band of a channel region 122A of the second transistor 120 and the second transistor 120 may serve as an N-type transistor.

The first glue layer GL1 is disposed on the overlying work function layer OWF and the second glue layer GL2 is disposed on the second work function layer WF2. In some alternative embodiments, one or more additional work function layers may be disposed between the overlying work function layer OWF and the first glue layer GL1 and/or one or more work function layers may be disposed between the second work function layer WF2 and the second glue layer GL1 based on various design requirements. The first glue layer GL1 and the second glue layer GL2 may be formed by a common glue layer and the material of the first glue layer GL1 and the second glue layer GL2 may include TiN or similar material. The first gate fill material GF1 and the second gate fill material GF2 disposed on the first glue layer GL1 and the second glue layer GL2 may be formed by the same layer of a gate fill material such as W, TiN, TaN, WN, Re, Ir, Ru, Mo, Al, Cu, Co, Ni, combinations thereof, and/or other suitable compositions. In some embodiments, the material of the first glue layer GL1 and the second glue layer GL2 may have desirable affinity to the material of the first gate fill material GF1 and the second gate fill material GF2, such that the first gate fill material GF1 and the second gate fill material GF2 may be firmly adhered to the first glue layer GL1 and the second glue layer GL2, respectively.

Figure 4:
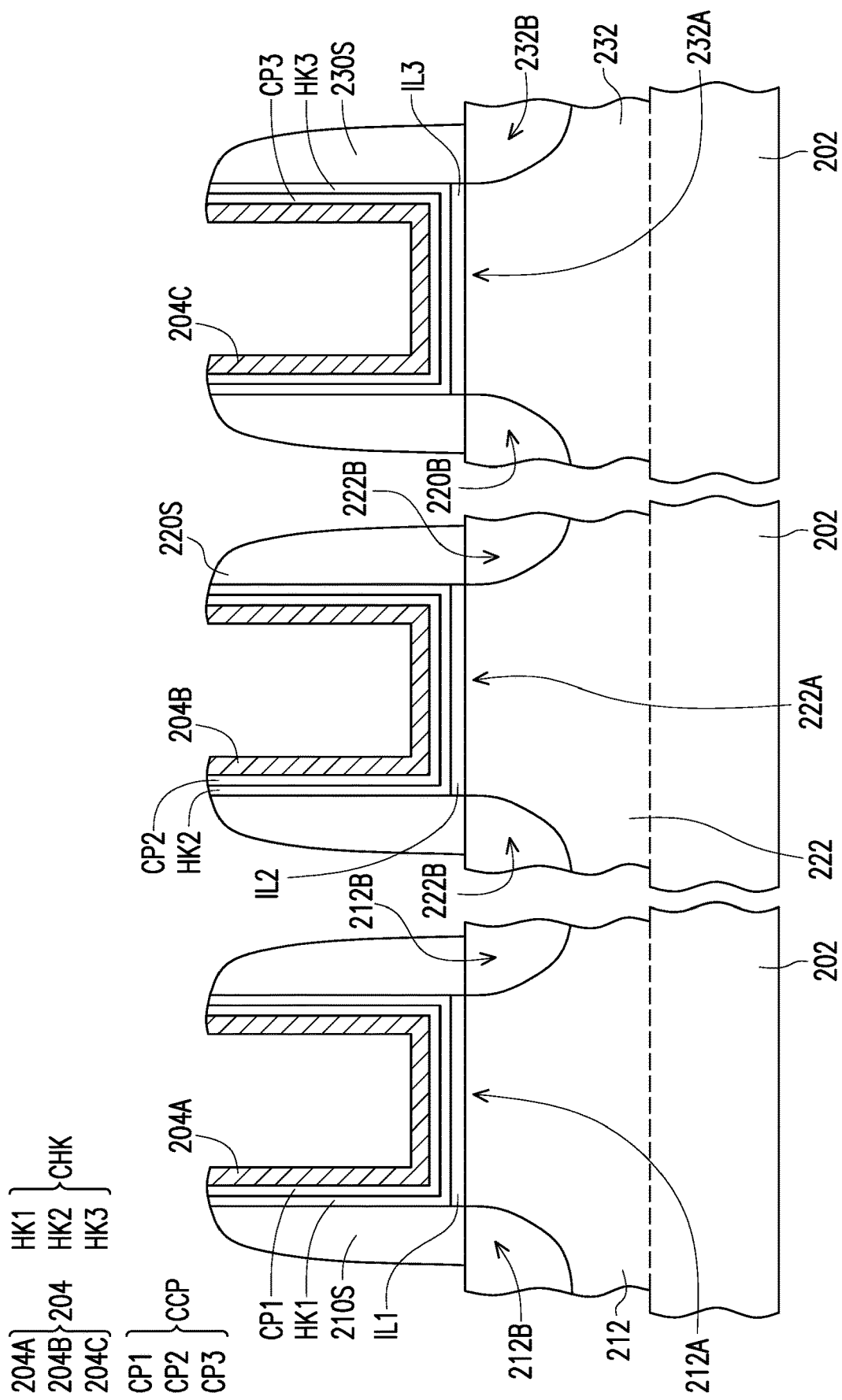
FIGS. 4-9 schematically illustrate a method of fabricating a semiconductor device in accordance with some embodiments.

FIGS. 4-9 schematically illustrate a method of fabricating a semiconductor device in accordance with some embodiments. In FIG. 4, semiconductor fins 212, 222, and 232 are formed on a substrate 202 and the substrate 202 is commonly shared by the semiconductor fins 212, 222, and 232. Each of the semiconductor fins 212, 222, and 232 may have a linear structure in the top view, which is similar to the top view structures of the first and second semiconductor fins 112 and 122 shown in FIG. 1. The semiconductor fin 212 may have a channel region 212A. Two doped regions 212B may be formed and located at opposite sides of the channel region 112A. The semiconductor fin 222 may have a channel region 222A interposed between two doped regions 222B, and the semiconductor fin 232 may have a channel region 232A sandwiched between two doped regions 232B.

An insulating layer IL1 may be formed on the channel region 212A of the semiconductor fin 212, an insulating layer IL2 may be formed on the channel region 222A of the semiconductor fin 222, and an insulating layer IL3 may be formed on the channel region 232A of the semiconductor fin 232. In some embodiments, a spacer 210S may be formed on the semiconductor fin 212 to form a recess structure over the semiconductor fin 212, a spacer 220S may be formed on the semiconductor fin 222 to form a recess structure over the semiconductor fin 222, and a spacer 230S may be formed on the semiconductor fin 232 to form a recess structure over the semiconductor fin 232. In some embodiments, the material of the inculsting layer IL1, the insulating layer IL2 and the insulating layer IL3 may include silicon oxide and/or silicon oxynitride and may be formed by chemical oxidation, thermal oxidation, atomic layer deposition (ALD), chemical vapor deposition (CVD), and/or alternative suitable methods.

A common high-k layer CHK is formed on the substrate 202 by using physical vapor deposition (PVD), atomic layer deposition (ALD), chemical vapor deposition (CVD), sputtering, or other known processes. The common high-k layer CHK may have a dielectric constant greater than, for example, about 2.9 (the dielectric constant of silicon dioxide) or about 7.0. In some examples, the material of the common high-k layer CHK includes hafnium oxide ($HfO_2$). Alternatively, the material of the common high-k layer CHK may include other high-k dielectrics, such as $TiO_2$, HfZrO, $Ta_2O_3$, $HfSiO_4$, $ZrO_2$, $ZrSiO_2$, LaO, AlO, ZrO, TiO, $Ta_2O_5$, $Y_2O_3$, $SrTiO_3$ (STO), $BaTiO_3$ (BTO), BaZrO, HfZrO, HfLaO, HfSiO, LaSiO, AlSiO, HfTaO, HfTiO, (Ba, Sr)$TiO_3$ (BST), $Al_2O_3$, $Si_3N_4$, oxynitrides (SiON), combinations thereof, or other suitable material. A portion of the common high-k layer CHK covers the recess structure of the spacer 210S in a conformed manner to serve as a first high-k layer HK1, a portion of the common high-k layer CHK covers the recess structure of the spacer 220S in a conformed manner to serve as a second high-k layer HK2, and a portion of the common high-k layer CHK covers the recess structure of the spacer 230S in a conformed manner to serve as a third high-k layer HK3. The first high-k layer HK1, the second high-k layer HK2 and the third high-k layer HK3 are formed of the same layer, the common high-k layer CHK, and may have the same material and the same thickness.

Next, a common capping layer CCP is formed on the common high-k layer CHK. The common capping layer CCP may be formed by depositing a high resistant material. In some embodiments, the material of the common capping layer CCP may include nitride, silicon nitride, carbon nitride, and/or aluminum nitride of titanium; a nitride, carbon nitride, and/or carbide of tungsten; the like; or a combination thereof. In some instances, the material of the common capping layer CCP may include titanium silicon nitride (TSN), titanium nitride (TiN), or the like. A portion of the common capping layer CCP covering the first high-k layer HK1 forms a first capping layer CP1, a portion of the common capping layer CCP covering the second high-k layer HK2 forms a second capping layer CP2, and a portion of the common capping layer CCP covering the third high-k layer HK3 forms a third capping layer CP3. The first capping layer CP1, the second capping layer CP2 and the third capping layer CP3 may be of the same layer, have the same material and have the same thickness.

A common work function layer 204 is then deposited on the common capping layer CCP. The material of the common work function layer 204 may include Ta. For example, the material of the common work function layer 204 may include TaN. The common work function layer 204 may include a portion 204A covering the first capping layer CP1, a portion 204B covering the second capping layer CP2, and a portion 204C covering the third capping layer CP3. In some embodiments, the work function of the common work function layer 204 may have a work function substantially aligned with a work function of the substrate valence band, or at least substantially aligned with a work function of the valence band of the channel region 232A.

Figure 5:
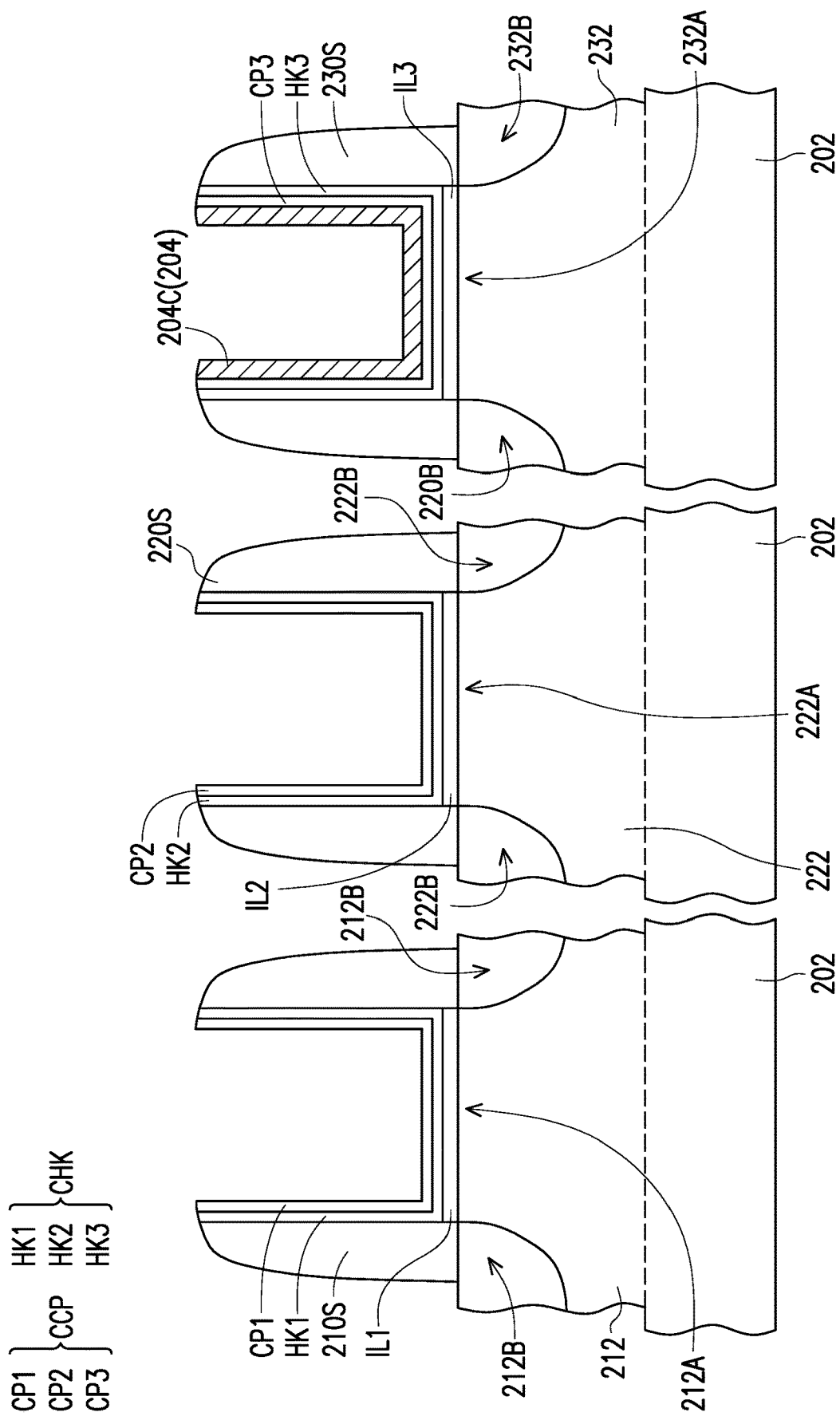

Referring to FIG. 4 and FIG. 5 together, the common work function layer 204 may be patterned by removing the portion 204A covering the first capping layer CP1 and the portion 204B covering the second capping layer CP2. The portion 204C remains on the third capping layer CP3. The etchant used for patterning the common work function layer 204 may have a good selectivity between the common work function layer 204 and the common capping layer CCP so as to prevent the common high-k layer CHK from unintentional damage. In some embodiments, the common work function layer 204 may be removed by using a halogen based etchant. In some embodiments, the halogen based etchant may include a Cl-based or F-based etchant. In some embodiments, the Cl-based or F-based etchant includes $TiCl_x$, $TaCl_x$, $TiF_x$, $HfCl_x$, $WF_x$, or $WCl_x$, where 'x' is equal to about 1-6. In some embodiments, the etchant used for patterning the common work function layer 204 of TaN may include $WCl_5$. The first capping layer CP1 and the second capping layer CP2 may be made of a material presenting higher resistant to $WCl_5$ than the common work function layer 204. The etching rate of the common work function layer 204 using TaN as etchant may be obviously higher than that of the first capping layer CP1 and the second capping layer CP2. The first capping layer CP1 and the second capping layer CP2 may be hardly removed by the halogen based etchant and serve as an etching stop during the process of patterning the common work function layer 208. Thus, the first high-k layer HK1 and the second high-k layer HK2 may not be damaged during the process of patterning the common work function layer 204 and present desirable dielectric property. In some embodiments, the material of the common high-k layer CHK may have an etching rate for the halogen based etchant between the common capping layer CCP and the common work function layer 204. In the case the common capping layer CCP is not interposed between the common high-k layer CHK and the common work function layer 204, the common capping layer CCP may be damaged during the patterning of the common work function layer 204.

Figure 6:
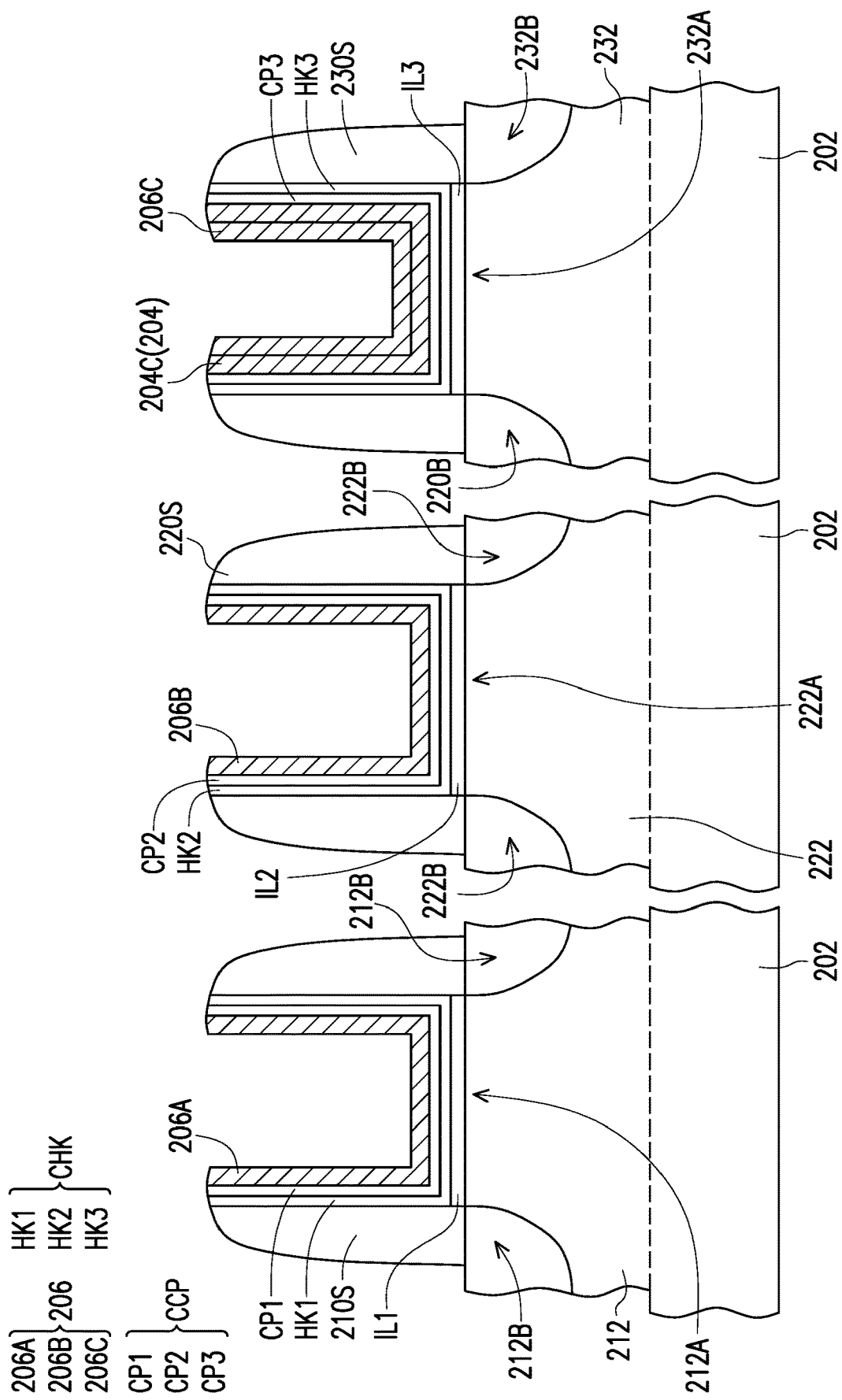

Referring to FIG. 6, another common work function layer 206 is formed on the substrate 202 after the first capping layer CP1 and the second capping layer CP2 are exposed. In some embodiments, the common work function layer 206 may be formed by using the same or similar method of forming the common work function layer 204 shown in FIG. 4. The material of the common work function layer 206 may include TaN. The common work function layer 206 includes a portion 206A covering the first capping layer CP1, a portion 206B covering the second capping layer CP2 and a portion 206C covering the remained portion 204C of the previously formed common work function layer 204 over the third capping layer CP3. In some embodiments, the work function of the common work function layer 206 may have a work function substantially aligned with a work function of the substrate valence band, or at least substantially aligned with a work function of the valence band of the channel region 212A.

Figure 7:
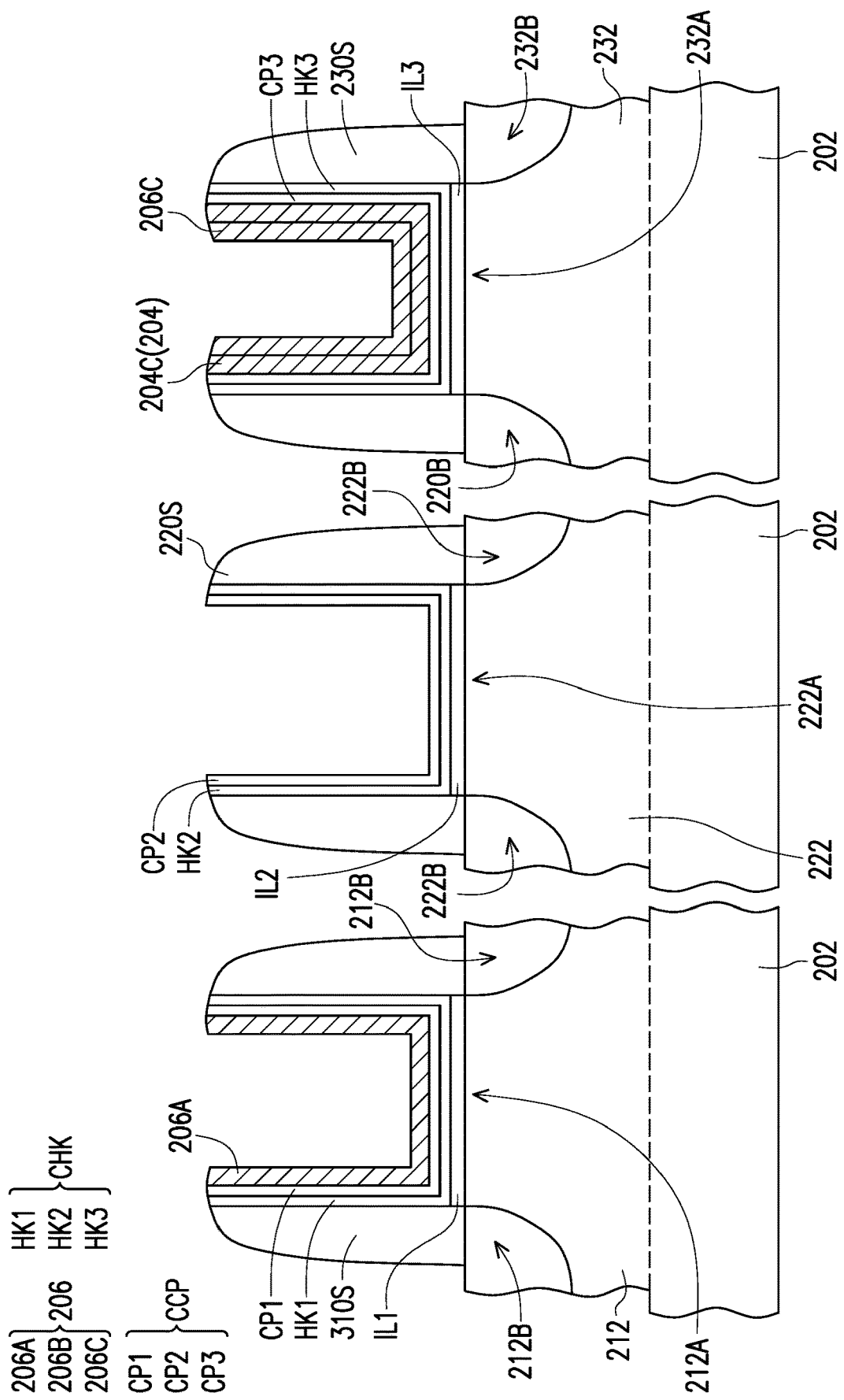

Referring FIG. 6 and FIG. 7 together, the common work function layer 206 may be patterned by removing the portion 206B covering the second capping layer CP2. The portion 206A of the common work function layer 206 may remain on the first capping layer CP1, and the portion 206C of the common work function layer 206 may remain on the portion 204C of the common work function layer 204. The process of patterning the common work function layer 206 may be similar to or the same as the process of patterning the common work function layer 204. In some embodiments, the Cl-based or F-based etchant including $TiCl_x$, $TaCl_x$, $TiF_x$, $HfCl_x$, $WF_x$, or $WCl_x$, where 'x' is equal to about 1-6 may be used for removing the portion 206B of the common work function layer 206. The process of patterning the common work function layer 206 may include removing the portion 206B of the common work function layer 206 until the second capping layer CP2 is exposed, for example, using $WCl_5$ as the etchant. In some embodiments, the second capping layer CP2 may present a low etching rate for the etchant of $WCl_5$ and thus may be hardly removed during the process of patterning the common work function layer 206 so as to protect the underlying second high-k layer HK2 from damage. Since the etchant used for patterning the common work function layer 206 may have a good selectivity between the common work function layer 206 and the second capping layer CP2, the thickness of the second capping layer CP2 may not be reduced and the second capping layer CP2 may serve as an etching stop during the process of patterning the common work function layer 206.

Figure 8:
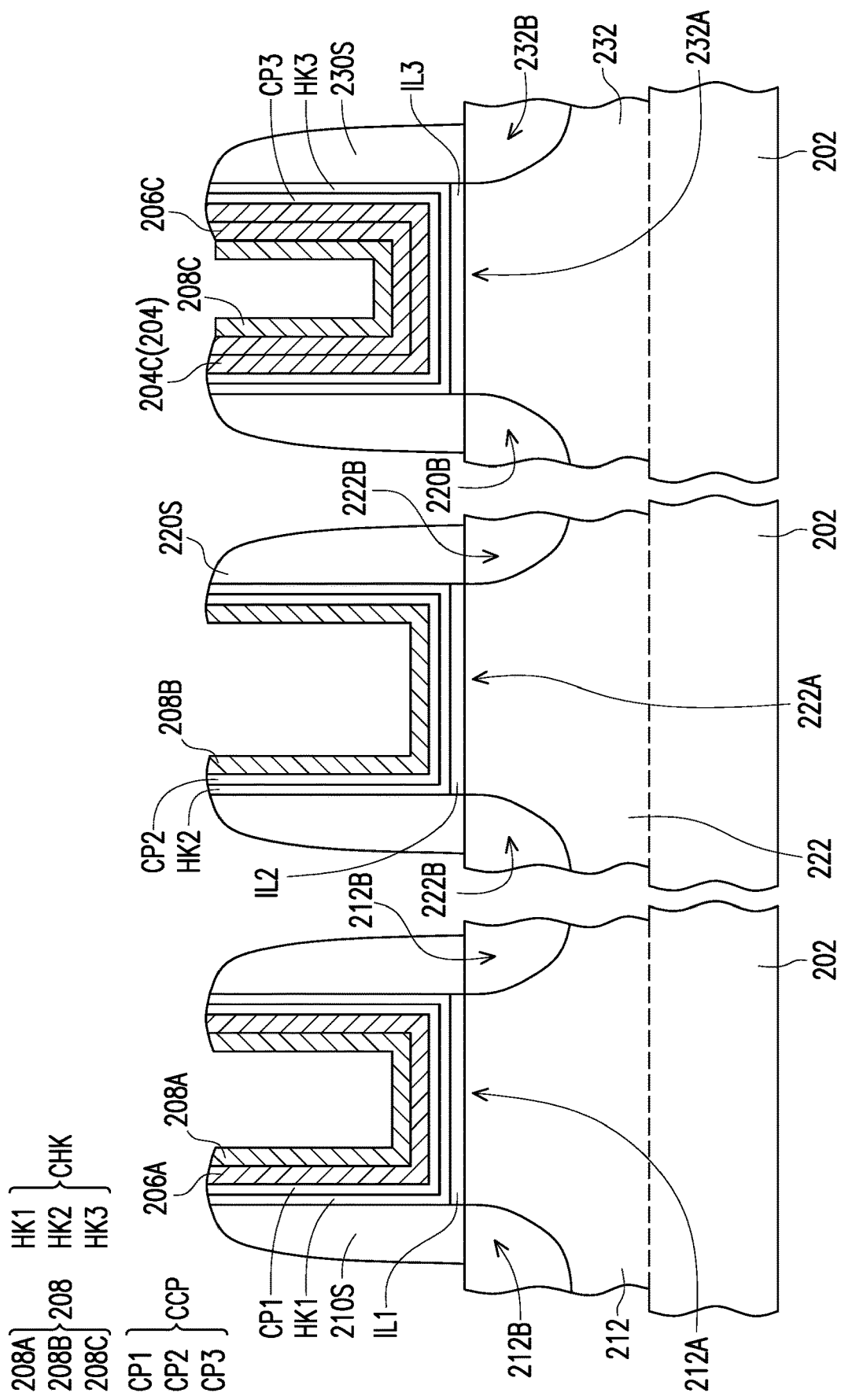

Referring to FIG. 8, a further common work function layer 208 may be formed on the substrate 202 by physical vapor deposition (PVD), atomic layer deposition (ALD), chemical vapor deposition (CVD), sputtering, or other known processes. The common work function layer 208 may include Al. The common work function layer 208 may be made of metal or metal carbide. In some embodiments, the material of the common work function layer 208 may include at least one selected from TiAl, TiAlC, TaC, TaAlC, NbC, and VC. In some embodiments, the material of the common work function layer 208 may include metals having a work function substantially aligned with a work function of the substrate conduction band, or at least substantially aligned with a work function of the conduction band of a channel region 232A. The previously formed common work function layers 204 and 206 may, but not limit thereto, have a work function greater than the common work function layer 208. In some embodiments, the common work function layers 204 and 206 may have a characteristic similar to p-type work function layer and the common work function layer 208 may have a characteristic similar to n-type work function layer, but is not limited thereto.

Figure 9:
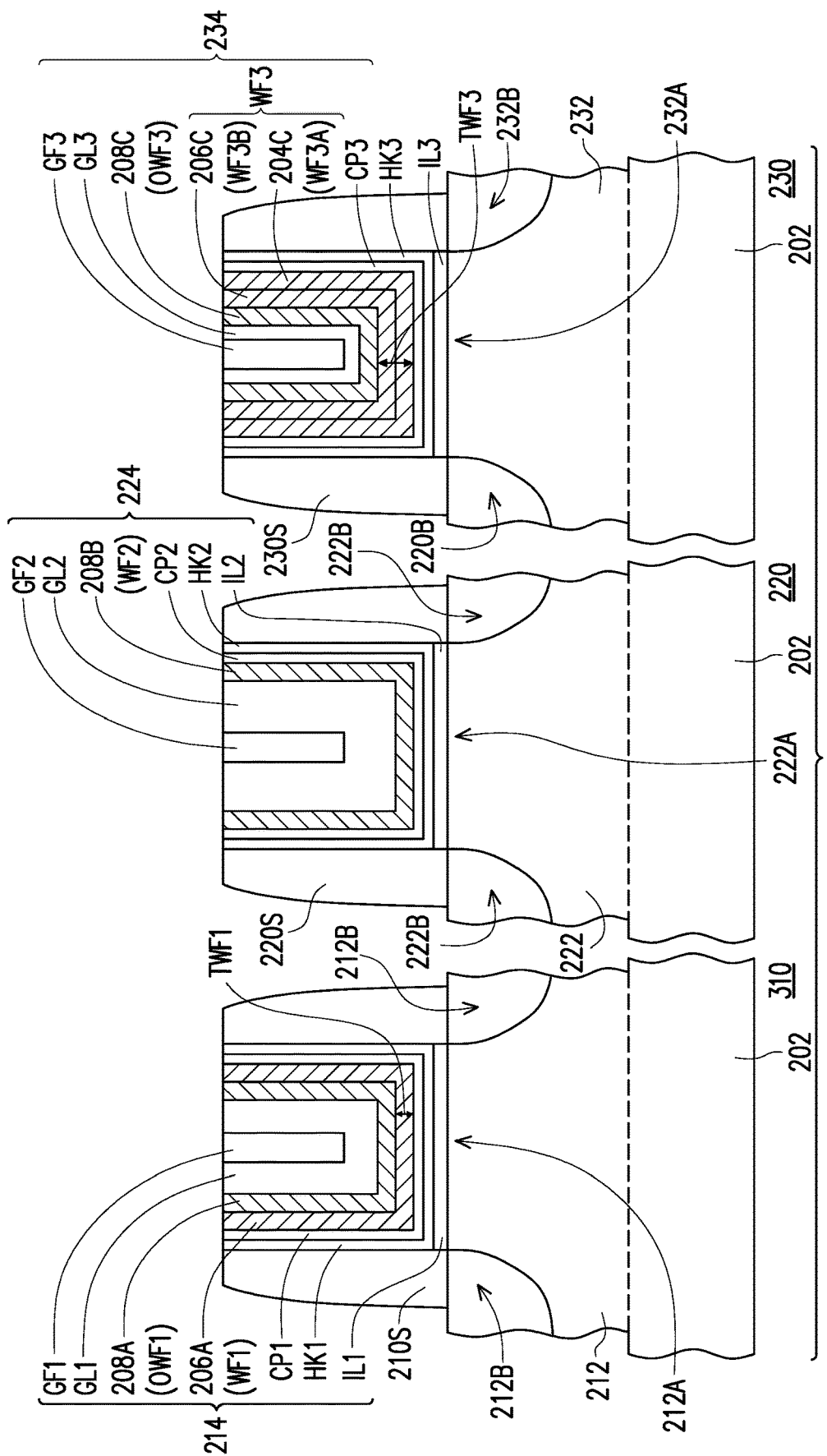

Referring to FIG. 8 and FIG. 9, a common glue layer and a common gate fill material are then sequentially formed on the substrate 202 after the patterning of the common work function layer 208. The common glue layer may form a first glue layer GL1 covering the portion 208A of the common work function layer 208, a second glue layer GL2 covering the portion 208B of the common work function layer 208, and a third glue layer GL3 covering the portion 208C of the common work function layer 208. The first glue layer GL1, the second glue layer GL2 and the third glue layer GL3 may be formed to define recess structures corresponding to the spaces 210S, 220S and 230S, respectively. The common gate fill material may form a first gate fill material GF1 filling the recess structure defined by the first glue layer GL1, a second gate fill material GF2 filling the recess structure defined by the second glue layer GL2, and a third gate fill material GF3 filling the recess structure defined by the third glue layer GL3. Subsequently, a planarization process such as chemical mechanical polishing (CMP) process may be performed to remove extra material to form individual gate structures 214, 224 and 234 respectively over the semiconductor fin 212, the semiconductor fin 222 and the semiconductor fin 232.

In the first gate structure 214, the portion 206A of the common work function layer 206 and the portion 208A of the common work function layer 208 sequentially covering the first capping layer CP1 may respectively serve as a first work function layer WF1 and an overlying work function layer OWF1. The first gate structure 214 may include the first high-k layer HK1, the first capping layer CP1, the first work function layer WF1, the overlying work function layer OWF1, the first glue layer GL1 and the first gate fill material GF1, wherein the first high-k layer HK1, the first capping layer CP1, the first work function layer WF1, the overlying work function layer OWF1, the first glue layer GL1 and the first gate fill material GF1 may form a common top surface for contacting with another conductive material or another component. The first work function layer WF1 and the overlying work function layer OWF1 may be made of different materials so as to determine and tune the threshold voltage of the transistor 210 having the first gate structure 214.

The portion 208B of the common work function layer 208 covering the second capping layer CP2 forms a second work function layer WF2 of the second gate structure 224. The second gate structure 224 may include the second high-k layer HK2, the second capping layer CP2, the second work function layer WF2, the second glue layer GL2 and the second gate fill material GF2, wherein the second high-k layer HK2, the second capping layer CP2, the second work function layer WF2, the second glue layer GL2 and the second gate fill material GF2 may form a common top surface for contacting with another conductive material or another component. The second work function layer WF2 serves to determine and tune the threshold voltage of the transistor 220 having the second gate structure 224. Since the work function of the second work function layer WF2 is different from the work function provided by the stacking of the first work function layer WF1 and the overlying work function layer OWF1, the transistor 210 having the first gate structure 214 and the transistor 220 having the second gate structure 224 may have different threshold voltages to achieve a multi-Vt (threshold voltage) design.

In the gate structure 234, the portion 204C of the common work function layer 204 and the portion 206C of the common work function layer 206 may respectively serve as a first sub layer WF3A and a second sub layer WF3B of a third work function layer WF3. The first sub layer WF3A and the second sub layer WF3 may be made of the same material so that the third function layer WF3 may be a thick work function layer with a thickness TWF3 greater than the thickness TWF1 of the first work function layer WF1 of the same material. In addition, the portion 208C of the common work function layer 208 covering over the third work function layer WF3 may serve as the overlying work function layer OWF3. The gate structure 234 may include the third high-k layer HK3, the third capping layer CP3, the third work function layer WF3, the overlying work function layer OWF3, the third glue layer GL3 and the third gate fill material GF3, wherein the third high-k layer HK3, the third work function layer WF3, the overlying work function layer OWF3, the third glue layer GL3 and the third gate fill material GF3 may form a common top surface for contacting with another conductive material or another component. The work function of the thick third work function layer WF3 may be different from that of the first work function layer WF1 so that the first gate structure 214 and the third gate structure 234 may be adopted to form the transistors with different threshold voltages so as to achieve a multi-Vt design.

The first gate structure 214, the second gate structure 224 and the third gate structure 234 respectively disposed over the semiconductor fin 212, the semiconductor fin 222 and the semiconductor fin 232 may construct transistors 210, 220 and 230 of a semiconductor device 200. The first gate structure 214, the second gate structure 224 and the third gate structure 234 may have different work function tuning design so that the transistors 210, 220 and 230 may have different threshold voltages so facilitate the application of multi functions semiconductor device.

As discussed above, the semiconductor device includes a patterned work function layer made of a material including Ta such as TaN and the patterned work function layer is disposed over the capping layer. A portion of the capping layer is not covered by the work function layer of TaN and may be exposed during the patterning of the work function layer of TaN. The work function layer of TaN may be patterned by using a halogen based etchant such as a Cl-based etchant or a F-based etchant. The etching rate of the work function layer of TaN may be higher than that of the capping layer so that the capping layer may not be thinned or removed during the patterning of the work function layer of TaN. In addition, the high-k layer underlying the capping layer may be protected from damage during the patterning process of the high-k layer. Accordingly, the patterned work function layer of TaN may be achieved without damaging the capping layer or the high-k layer. The semiconductor device having the patterned work function layer may achieve multi voltages device design.

In accordance with some embodiments of the disclosure, a semiconductor device may include a substrate, a first transistor disposed on the substrate, and a second transistor disposed on the substrate. The first gate structure of the first transistor may include a first high-k layer, a first capping layer and a first work function layer sequentially disposed on the substrate, wherein a material of the first work function layer includes Ta. The second transistor includes a second gate structure. The second gate structure includes a second high-k layer, a second capping layer and a second work function layer sequentially disposed on the substrate, wherein the first capping layer and the second capping layer are formed of the same layer, and a material of the second work function layer is different from the material of the first work function layer.

In accordance with some embodiments of the disclosure, a semiconductor device may include a substrate, a first transistor disposed on the substrate, and a second transistor disposed on the substrate. The first transistor includes a first gate structure, wherein the first gate structure may include a first high-k layer, a first capping layer and a first work function layer sequentially disposed on the substrate. The second transistor may include a second gate structure, wherein the second gate structure includes a second high-k layer, a second capping layer and a second work function layer sequentially disposed on the substrate. A material of the first work function layer is different from a material of the second work function layer, and the material of the second high-k layer presents an etching rate for a halogen based etchant between the material of the first work function layer and a material of the second capping layer.

In accordance with some embodiments of the disclosure, a semiconductor device may include a substrate, a first gate structure disposed on the substrate, and a second gate structure disposed on the substrate. The first gate structure includes a first high-k layer, a first capping layer, a first work function layer and an overlying work function layer sequentially disposed on the substrate, wherein the first work function layer is in direct contact with the first capping layer, and a material of the first work function layer includes Ta. The second gate structure includes a second high-k layer, a second capping layer and a second work function layer sequentially disposed on the substrate, wherein the second work function layer is in direct contact with the second capping layer and is formed of the same layer as the overlying work function layer.

In accordance with some embodiments of the disclosure, the material of the first work function layer may include TaN, HfN, WN, or the like. The material of the first work function layer has a higher etching rate for a halogen based etchant than a material of the second capping layer. The material of the first capping layer and the second capping layer may include TiSiN, TiN, TiAlN, or the like. A material of the second work function layer may include aluminum, and for example, the material of the second work function layer comprises TiAl, TiAlC, TaAl, TaAlC, or the like. The first transistor further includes an overlying work function layer disposed on the first work function layer and a material of the overlying work function layer is the same as the material of the second work function layer. The semiconductor device may further include a third transistor disposed on the substrate. The third transistor may include a third gate structure, wherein the third gate structure includes a third high-k layer, a third capping layer, and a third work function layer sequentially disposed on the substrate, a material of the third work function layer is the same as the material of the first work function layer, and a thickness of the third work function layer is different from a thickness of the first work function layer.

In accordance with some embodiments of the disclosure, the halogen based etchant may include $WCl_5$. A work function of the first work function layer may be greater than a work function of the second work function layer. A material of the first capping layer and a material of the second capping layer may include Ti—Si—N, TiN, TiAlN, or the like. The material of the second work function layer may include TiAl, TiAlC, TaAl, TaAlC, or the like.

In accordance with some embodiments of the disclosure, a work function of the first work function layer is greater than a work function of the second work function layer. A material of the first work function layer has a higher etching rate for a halogen based etchant than a material of the second capping layer. The halogen based etchant may include Cl-based etchant or F-based etchant. The halogen based etchant may include $WCl_5$. The material of the first capping layer and the second capping layer may include Ti—Si—N, TiN, TiAlN, or the like. A material of the second work function layer may include TiAl, TiAlC, TaAl, TaAlC, or the like.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor device, comprising:
   a substrate;
   a first transistor disposed on the substrate, and comprising a first gate structure, wherein the first gate structure comprises a first high-k layer, a first capping layer, a first work function layer and an overlying work function layer sequentially disposed on the substrate, wherein a material of the first work function layer comprises Ta, and the overlying work function layer is in direct contact with the first work function layer; and
   a second transistor disposed on the substrate, and comprising a second gate structure, the second gate structure comprising a second high-k layer, a second capping layer and a second work function layer sequentially disposed on the substrate, the second work function layer being in direct contact with the second capping layer, wherein the first capping layer and the second capping layer are formed of the same layer, a material of the second work function layer is different from the material of the first work function layer, and the overlying work function layer and the second work function layer are of the same layer.

2. The semiconductor device of claim 1, wherein the material of the first work function layer comprises TaN, HfN, WN, or a combination thereof.

3. The semiconductor device of claim 1, wherein the material of the first work function layer has a higher etching rate for a halogen based etchant than a material of the second capping layer.

4. The semiconductor device of claim 1, wherein the material of the first capping layer and the second capping layer comprises TiSiN, TiN, TiAlN, or a combination thereof.

5. The semiconductor device of claim 1, wherein the material of the second work function layer comprises aluminum.

6. The semiconductor device of claim 5, wherein the material of the second work function layer comprises TiAl, TiAlC, TaAl, TaAlC, or a combination thereof.

7. The semiconductor device of claim 1, wherein the first transistor further comprises a first glue layer disposed on the overlying work function layer.

8. The semiconductor device of claim 1, further comprising:
   a third transistor disposed on the substrate, and comprising a third gate structure, wherein the third gate structure comprises a third high-k layer, a third capping layer, and a third work function layer sequentially disposed on the substrate, a material of the third work function layer is the same as the material of the first work function layer, and a thickness of the third work function layer is different from a thickness of the first work function layer.

9. A semiconductor device, comprising:
   a substrate; and
   a first transistor disposed on the substrate, and comprising a first gate structure, wherein the first gate structure comprises a first high-k layer, a first capping layer, a first work function layer and an overlying work function layer sequentially disposed on the substrate the first capping layer being in direct contact with the first high-k layer, and the overlying work function layer is in direct contact with the first work function layer; and a second transistor disposed on the substrate, and comprising a second gate structure, wherein the second gate structure comprises a second high-k layer, a second capping layer and a second work function layer sequentially disposed on the substrate, the second capping layer being in direct contact with the second high-k layer, a material of the first work function layer is different from a material of the second work function layer, the overlying work function layer and the second work function layer are of the same layer, and a material of the second high-k layer presents an etching rate for a halogen based etchant between the material of the first work function layer and a material of the second capping layer.

10. The semiconductor device of claim 9, wherein the halogen based etchant comprises $WCl_5$.

11. The semiconductor device of claim 9, wherein a work function of the first work function layer is greater than a work function of the second work function layer.

12. The semiconductor device of claim 9, wherein a material of the first capping layer and the material of the second capping layer comprise Ti—Si—N, TiN, TiAlN, or a combination thereof.

13. The semiconductor device of claim 9, wherein the material of the second work function layer comprises TiAl, TiAlC, TaAl, TaAlC, or a combination thereof.

14. A semiconductor device, comprising:
a substrate;
a first gate structure disposed on the substrate and comprising a first high-k layer, a first capping layer, a first work function layer and an overlying work function layer sequentially disposed on the substrate, wherein the first work function layer is in direct contact with the first capping layer, the overlying work function layer is in direct contact with the first work function layer, and a material of the first work function layer comprises Ta; and
a second gate structure disposed on the substrate and comprising a second high-k layer, a second capping layer and a second work function layer sequentially disposed on the substrate, the second capping layer being in direct contact with the second high-k layer, wherein the second work function layer is in direct contact with the second capping layer and is formed of the same layer as the overlying work function layer.

15. The semiconductor device of claim 14, wherein a work function of the first work function layer is greater than a work function of the second work function layer.

16. The semiconductor device of claim 14, wherein a material of the first work function layer has a higher etching rate for a halogen based etchant than a material of the second capping layer.

17. The semiconductor device of claim 16, wherein the halogen based etchant comprises Cl-based etchant or F-based etchant.

18. The semiconductor device of claim 16, wherein the halogen based etchant comprises $WCl_5$.

19. The semiconductor device of claim 14, wherein the material of the first capping layer and the second capping layer comprises Ti—Si—N, TiN, TiAlN, or a combination thereof.

20. The semiconductor device of claim 14, wherein a material of the second work function layer comprises TiAl, TiAlC, TaAl, TaAlC, or a combination thereof.

* * * * *